United States Patent [19]
Mellins

[11] Patent Number: 5,985,547
[45] Date of Patent: Nov. 16, 1999

[54] DETECTION OF A MUTATION IN THE HLA-DMβ GENE IN AN IMMUNOCOMPROMISED PATIENT

[75] Inventor: Elizabeth D. Mellins, Wynnewood, Pa.

[73] Assignee: Children's Hospital of Philadelphia, Philadelphia, Pa.

[21] Appl. No.: 08/206,790

[22] Filed: Mar. 4, 1994

[51] Int. Cl.[6] .............................. C12Q 1/68; C07H 21/02; C07H 21/04
[52] U.S. Cl. ............................. 435/6; 536/23.1; 536/24.3
[58] Field of Search ................................ 435/6; 536/23.1, 536/24.3; 935/77, 78

[56] References Cited

PUBLICATIONS

Brown, et al., "Three-Dimensional Structure of the Human Class II Histocompatibility Antigen HLA-DR1", *Nature* (1993) 364:33–39.
Calabretta et al., "The Laboratory-Clinic Interface: Prospects for Gene-Directed Therapy With Antisense Oligodeoxynucleotides", *Cancer Treatment Reviews* (1993) 19:169–179.
Cammarota, et al., "Identification of a CD4 Binding Site on the $\beta_2$ Domain of HLA-DR Molecules", *Nature* (1992) 356:799–801.
Ceman, et al., "MHC Class II Deletion Mutant Expresses Normal Levels of Transgene Encoded Class II Molecules That Have Abnormal Conformation and Impaired Antigen Presentation Ability", *J. Immun.* (1992) 149:754–761.
Chicz, et al., "Specificity and Promiscuity Among Naturally Processed Peptides Bound to HLA-DR Alleles", *J. Exp. Med.* (1993) 178:27–47.
Chicz, et al., "Predominant Naturally Processed Peptides Bound to HLA-DR1 are Derived From MHC-Related Molecules and are Heterogeneous in Size", *Nature* (1992) 358:764–768.
Cho, et al., "New Class II-Like Genes in the Muring MHC", *Nature* (1991) 353:573–576.
Hansen, et al., *Leukocyte Typing* (1984) (eds. Bernard, A., Boumsell, L., Dausset, J., Milstein, C. and Schlossman, S.) 195 (Springer, Heidelberg).
Cosgrove, et al., "Mice Lacking MHC Class II Molecules", *Cell* (1991) 66:1051–1066.
Germain, et al., "MHC Class II Structure, Occupancy and Surface Expression Determined By Post-Endoplasmic Reticulum Antigen Binding", *Nature* (1991) 353:134–139.
Gewirtz, A.M., *Leukemia and Lymphoma* (1993) 11:131–137.
Griffith, et al., "Structural Mutation Affecting Intracellular Transport and Cell Surface Expression of Murine Class II Molecules", *J. Exp. Med.* (1988) 167:541–555.
Grusby, et al., "Depletion of CD4[+] T Cells in Major Histocompatibility Complex Class II-Deficient Mice", *Science* (1991) 253:1417–1720.
Guy, et al., "Differential Expression and Serologically Distinct Subpopulations of Human Ia Antigens Detected With Monoclonal Antibodies to Ia Alpha and Beta Chains", *Eur. J. Immun.* (1982) 12:942–948.

Harris, E. D., "Rheumatoid Arthritis", *New Eng. Jour. Med.* (1990) 322:1277–1289.
Hunt, et al., "Peptides Presented to the Immune System by the Murine Class II Major Histocompatibility Complex Molecule I-A$^{d}$", *Science* (1992) 256:1817–1820.
Johnson, et al., "Direct Demonstration of an HLA-DR Allotypic Determinant on the Low Molecular Weight (Beta) Subunit Using a Mouse Monoclonal Antibody Specific for DR3", *J. Exp. Med.* (1982) 156:104–111.
Johnson, et al., *ImmunoBiology of HLA* (ed. Dupont, B.O.) (Springer, New York, 1984).
Kelly, et al., "A New Human HLA Class II-Related Locus, DM", *J. Nature* (1991) 353:571–573.
Konig, et al., "MHC Class II Interaction With CD4 Mediated By a Region Analogous to the MHC Class I Binding Site for CD8", *Nature* (1992) 356:796–798.
Lampson, et al., "Two Populations of Ia-Like Molecules on a Human B Cell Line", *J. Immun.* (1980) 125:293–299.
Levine, et al., "Deletion Mapping of HLA and Chromosome 6p Genes", *Proc. Natl. Acad. Sci. U.S.A.*, (1985) 88:3741–3745.
Marsh et al., "HLA Class II Nucleotide Sequences, 1992", *Human Immunology* (1992) 35:1–17.
Mellins, et al., "Defective Processing and Presentation of Exogenous Antigens in Mutants With Normal HLA Class II Genes", *Nature* (1990) 343:71–74.
Mellins, et al., "A Gene Required for Class II-Restricted Antigen Presentation Maps to the Major Histocompatibility Complex", *J. Exp. Med.* (1991) 174:1607–1615.
Mellins, et al., "A Mutant Human Histocompatibility Leukocyte Antigen DR Molecule Associated With Invariant Chain Peptides", *J. Exp. Med.* (1994) 179:541–549.
Mellins, et al., "Importance of HLA-DQ and -DP Restriction Elements in T-Cell Responses to Soluble Antigens: Mutational Analysis", *Hum. Immun.* (1987) 18:211–223.
Miller, A. Dusty, "Human Gene Therapy Comes of Age", *Nature* (1992) 357:455.
Neefjes, et al., *EMBO J.* (1992) 11:411–416.
Oldstone et al., "Virus Infection Triggers Insulin-Dependent Diabetes Mellitus in a Transgenic Model: Role of Anti-Self (Virus) Immune Response", *Cell* (1991) 65:319–331.
Orita et al., "Rapid and Sensitive Detection of Point Mutations and DNA Polymorphisms Using the Polymerase Chain Reaction", *Genomics* (1989) 5:874–879.
Pious, et al., "HLA Class II Regulation and Structure", *J. Exp. Med.* (1985) 162:1193–1207.

(List continued on next page.)

*Primary Examiner*—W. Gary Jones
*Assistant Examiner*—Ethan Whisenant
*Attorney, Agent, or Firm*—Woodcock Washburn Kurtz Mackiewicz & Norris, LLP

[57] ABSTRACT

The identification of a mutation in the HLA-DMB locus in antigen presenting cells defective in presenting antigen is described. Methods of diagnosis and treatment of immunocompromised individuals and compositions and methods of treatment for patients suffering from autoimmune diseases are also described.

5 Claims, 14 Drawing Sheets

OTHER PUBLICATIONS

Ratajczak et al., "In Vivo Treatment of Human Leukemia in a Scid Mouse Model With c–myb Antisense Oligodeoxynucleotides", *Proc. Nat. Acad. Sci. USA* (1992) 89:11823–27.

Riberdy, et al., "HLA–DR Molecules From An Antigen–Processing Mutant Cell Line Are Associated With Invariant Chain Peptides", *Nature* (1992) 360:474–477.

Sant, et al., "MHC Class II Molecules Express A Targeting Signal That Directs Localization to the Endocytic Compartments of Antigen Presenting Cells", *Hum. Immun.* (1993) 37s:3.

Sette, et al., "Invariant Chain Peptides in Most HLA–DR Molecules of an Antigen–Processing Mutant", *Science* (1992) 258:1801–1804.

Xie, et al., "Rapid, Small–Scale RNA Isolation From Tissue Culture Cells", *Bio Techniques*, (1991) 11:325–327.

Fling, S.P. et al., "HLA–DMA and –DMB Genes are Both Required for MHC Class II–peptide Complex Formation in Antigen–presenting Cells", *Biological Abstracts* 1994, vol. 097, Issue 011, Ref. 155379 of *Nature vol. 368*, pp. 554–558, provided as Biosis No.:97238265.

Morris, P. et al., "An Essential Roel for HLA–DM in Antigen Presentation by Class II Major Histocompatibility Molecules", *Biological Abstracts* 1994, vol. 097, Issue 011, Ref. 155378 of *Nature vol. 368*, pp. 551–554, provided as Biosis No.:97238268.

Sanderson, F. et al., "Accumulation of HLA–DM, a Regulator of Antigen Presentation, in MHC Class II Compartments", *Science* 1994, 266, 1566–1569, provided as Medline No: 09146278 95076278.

Carrington, et al., Characterization of HLA–DMB polymorphism, Immunogenics 38:446–449 (1993).

Carrington et al. Immunogenetics 38:446–449 (1993).

Nocera et al. Human Immunology 38:231–234(1993).

"Basic Methods in Molecular Biology" Elsevier Science Publishing, Inc., Ed. Davis et al., pp. 62–65 and 143–146 (1986).

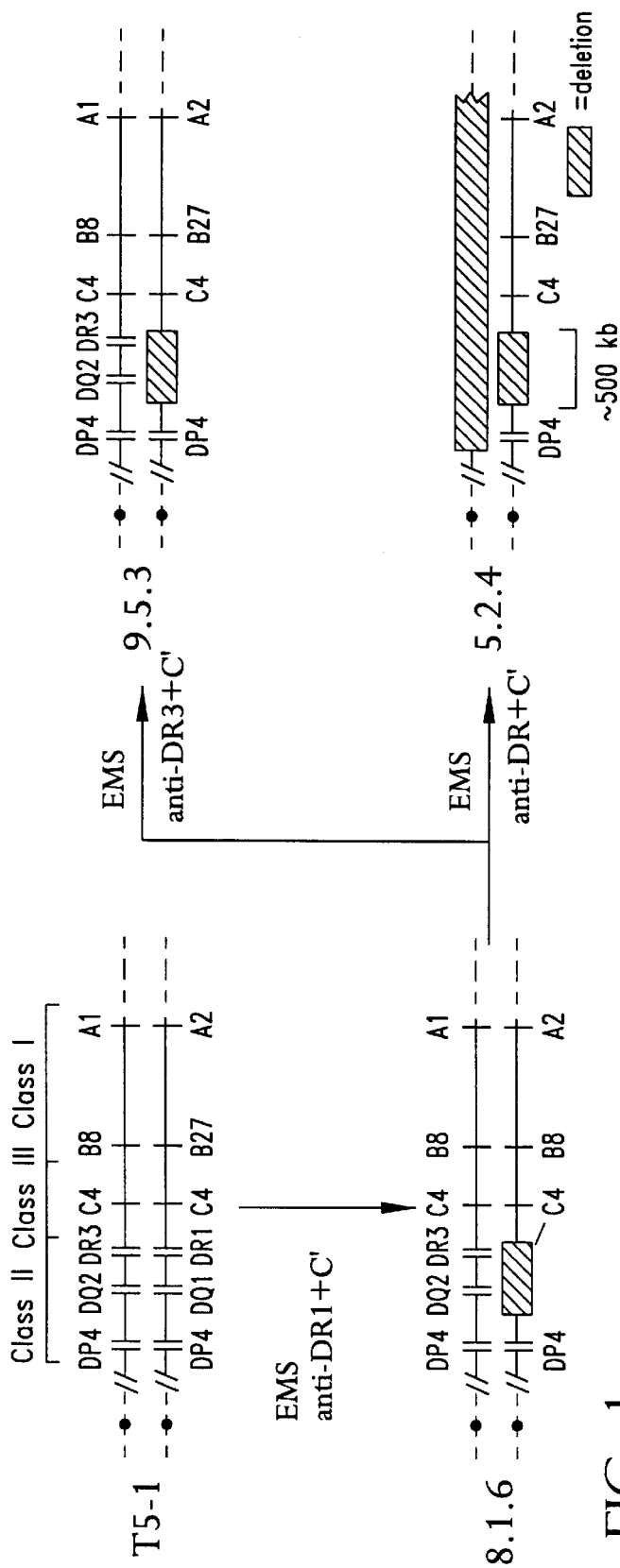
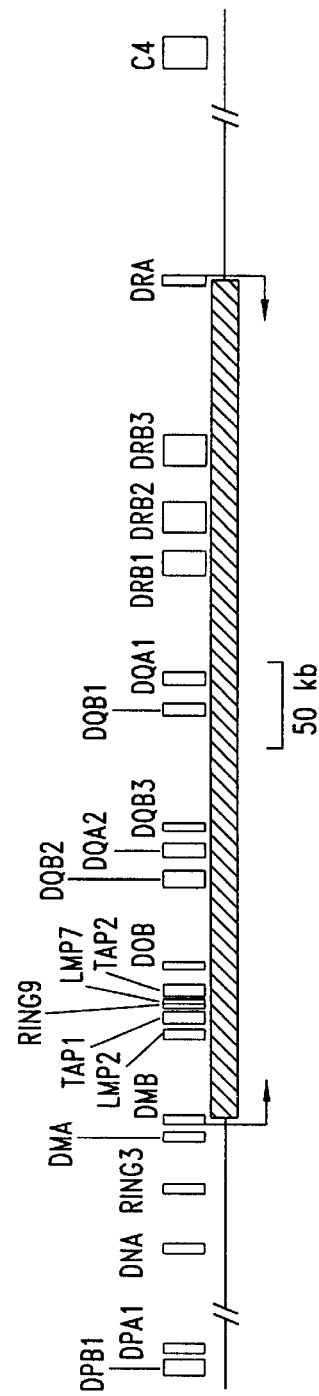
FIG. 1
FIG. 2

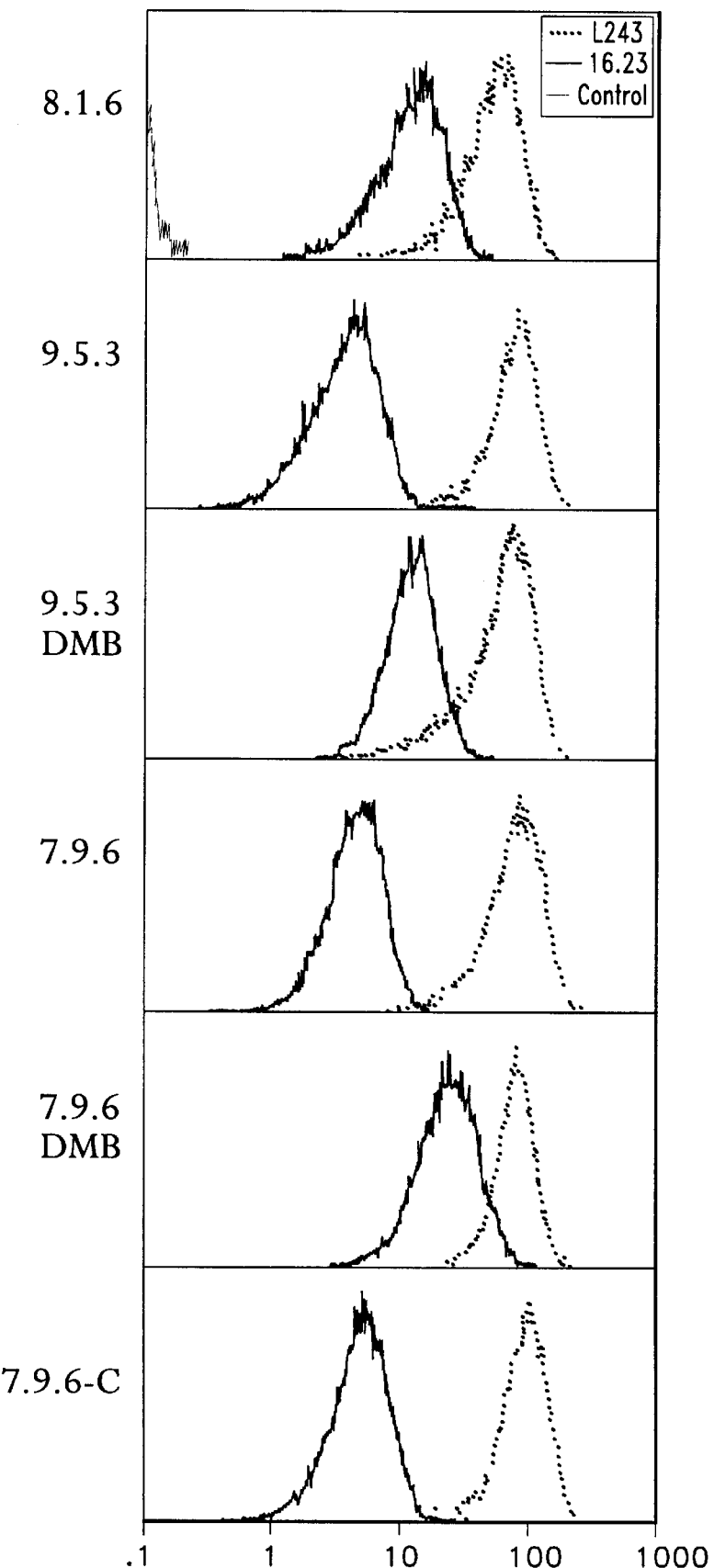
FIG. 9A  8.1.6
FIG. 9B  9.5.3
FIG. 9C  9.5.3 DMB
FIG. 9D  7.9.6
FIG. 9E  7.9.6 DMB
FIG. 9F  7.9.6-C

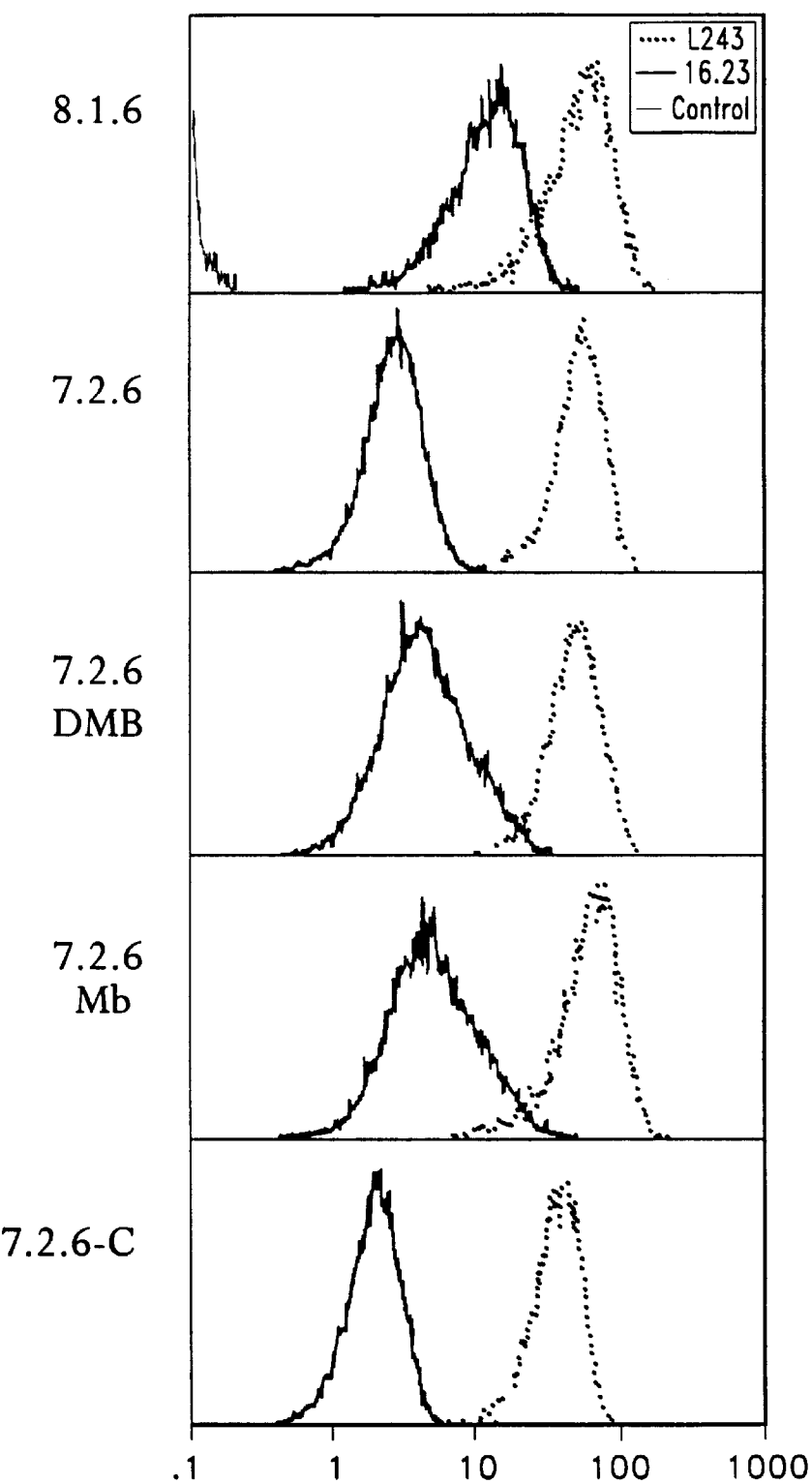
FIG. 9G  8.1.6
FIG. 9H  7.2.6
FIG. 9I  7.2.6 DMB
FIG. 9J  7.2.6 Mb
FIG. 9K  7.2.6-C

DETECTION OF A MUTATION IN THE HLA-DMβ GENE IN AN IMMUNOCOMPROMISED PATIENT

The invention was made with Government support. The Government may have certain rights in the subject invention.

TECHNICAL FIELD OF THE INVENTION

The present invention relates to the identification of a mutation in the HLA-DMB locus.

BACKGROUND OF THE INVENTION

In antigen presenting cells, class II molecules of the major histocompatibility complex (MHC) form complexes with peptides derived from endocytosed proteins. Class II molecules of the major histocompatibility complex (MHC) are heterodimeric (α/β), transmembrane glycoproteins expressed by antigen presenting cells (APC) of the immune system (e.g., macrophages, dendritic cells, B cells). Within APC, class II molecules bind peptides derived from endocytosed proteins and from other sources, and the MHC class II/peptide complex is expressed at the cell surface for surveillance by CD4+ T cells. Recognition by the T cell receptor of an antigenic MHC/peptide complex activates the T cell and initiates an immune response.

In human B-lymphoblastoid cell lines, the primary pathway for generating class II molecule/peptide complexes is intimately related to class II molecule biosynthesis. In the endoplasmic reticulum (ER), nascent class II heterodimers associate with the invariant chain (Ii), a class II molecule chaperon; this association promotes correct folding of class II molecules and prevents class II molecule acquisition of peptides in the ER. A targeting or retention signal within the cytoplasmic tail of invariant chain mediates localization of the class II/Ii complex to the endocytic pathway. After cleavage and dissociation of invariant chain, class II molecules bind peptides available in the endocytic pathway, and then traffick to the cell surface.

It had been postulated that the invariant chain may not be the only molecule functioning in this capacity. The requirement for another molecule in this pathway in addition to invariant chain can be inferred from data obtained with mutant human B lymphoblastoid cell lines (B-LCLs). A key feature of these mutants is a defect in presentation in intact protein antigen, but not immunogenic peptides, to class II restricted T cells. In addition, class II molecules expressed by the mutants fail to acquire features of the mature, peptide-loaded molecules of the progenitor cell, such as expression of certain antibody epitopes (e.g., mAb 16.23) and stability in SDS detergent solutions. (Neefjes, et al., *EMBO J.* (1992) 11:411–416; Mellins, et al., *Nature* (1990) 343:71–74; and Germain, et al., *Nature* (1991) 353:134–139, all incorporated herein by reference.) These observations suggested that the mutants are impaired in formation of complexes between class II molecules and peptides derived from endocytosed proteins.

This conclusion regarding the B-LCL mutants is confirmed by direct assessment of the peptides found in association with HLA-DR molecules—human molecules homologous to mouse class II molecules—in the mutants. Rather than the heterogeneous mixture of peptides found in wild type cells, the majority (60–70%) of the DR molecules expressed by the mutants are associated with a nested set of peptides from residues 80–103 of the invariant chain. (Mellins, et al., *J. Exp. Med.* (in the press); Riberdy, et al., *Nature* (1992) 360:474–477 and Sette, et al., *Science* (1992) 258:1801–1804, all incorporated herein by reference.) Though undetectable in the progenitor cell, these Ii peptides have been found in association with class II molecules in other wild type cells (Hunt, et al., *Science* (1992) 256:1817–1820; Chicz, et al., *Nature* (1992) 358:764–768 and Chicz, et al., *J. Exp. Med.* (1993) 178:27–47, all incorporated herein by reference), raising the possibility that the class II/Ii peptide complex is a biosynthetic intermediate. The mutant phenotype thus suggested a number of possible functions for the gene product altered in these cells, including generation or transport of peptides, chaperoning of class II molecules to peptide-containing compartments, or a function that directly facilitates peptide loading of class II molecules, such as removal of Ii peptides.

Although the specific role of its product has not been identified, the relevant gene has been mapped by the present inventor and is reported upon here. The derivation of the mutants from a progenitor cell that is hemizygous for the class II region of the MHC (see 8.1.6, FIG. 1 and Levine, et al., *Proc. Natl. Acad. Sci. U.S.A.*, (1985) 88:3741–3745, incorporated herein by reference) suggested that the responsible gene(s) mapped to this region. B-LCL mutants with homozygous deletions of the region, including the 8.1.6-derived mutant 5.2.4 (FIG. 1 and Mellins, et al., *J. Exp. Med.* (1991) 174:1607–1615, incorporated herein by reference), were found to share the class II presentation defect, confirming location of the relevant gene(s) within the MHC (Mellins, et al., (1991), supra and Ceman, et al., *J. Immun.* (1992) 149:754–761, incorporated herein by reference). The gene that underlies the mutant phenotype has been identified as HLA-DMB, an human MHC-linked gene that encodes a class II-like β chain. The results reported below establish HLA-DMB as a critical regulatory molecule in class II restricted antigen presentation and suggest that it functions at an intracellular site to promote class II molecule/peptide association. Transfection of mutants with DMB complementary DNA restored the wild type phenotype, establishing HLA-DM as a critical molecule in antigen presentation to CD4+ T cells.

SUMMARY OF THE INVENTION

In one aspect, the present invention relates to a method for determining a mutation in the HLA-DMB locus as a potential causative factor in an individual assessed as being immunocompromised. The method involves the isolation of nucleic acid from the B-lymphocytes of the immunocompromised individual and identifying mutations in HLA-DMB by any currently available means.

In another aspect, the present invention relates to a method for treating immunocompromised individuals who have been determined to harbor a mutation in HLA-DMB involving the administration of HLA-DMB nucleic acid which complements the defect.

In a further aspect, the present invention involves a method for treating a patient suffering from an autoimmune disease involving the administration of an agent that inhibits the function of DMβ to the specific tissue affected.

In yet a another aspect, the present invention involves a composition comprising an agent that inhibits the function of DMβ.

In yet a further aspect, the present invention involves an in vitro assay for assessing the relationship, if any, between antigen presentation and a known step in the pathophysiology of an autoimmune disease.

BRIEF DESCRIPTION OF THE DRAWINGS

FIG. 1 depicts the derivation of cell lines 8.1.6, 9.5.3, and 5.2.4 from B-lymphoblastoid line T5-1.

FIG. 2 depicts the expanded Genetic Map of the 8.1.6 deletion.

FIGS. 9A–9K depict the binding of mutant cell lines by antibodies 16.23 and L243 after transfection with DMB cDNA.

FIGS. 13A-13B depict the location of the primers used for performing sequence analyses.

DETAILED DESCRIPTION OF THE INVENTION

Figures 3A, 3B, 3C:
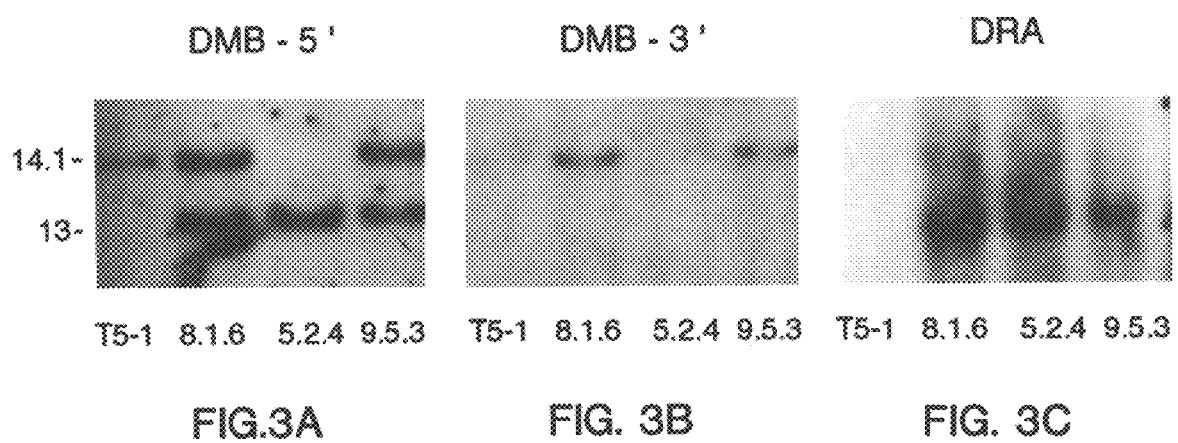
FIGS. 3A–3C depict Southern blot analyses of the 8.1.6 deletion breakpoints probed with DMB-5', DMB-3', and DRA, respectively.

According to the present invention, a defect in antigen presentation by conventional HLA class II molecules results from a mutation in HLA-DMB. The sequence of the HLA-DMB gene was obtained previously and suggests that it encodes a class II-like β chain; the linked HLA-DMA locus encodes a class II-like α chain, implying that the products of these genes may associate to form a heterodimer. (Kelly, et al., *J. Nature* (1991) 353:571–573, incorporated herein by reference.) However, the proposed DM molecule and its murine homologue Ma/Mb differ from other class II MHC molecules in several respects.

The putative membrane distal domain of HLA-DM shows limited sequence similarity to the corresponding domains of other class II molecules (14–25%). (Kelly, et al., supra and Cho, et al., *Nature* (1991) 353:573–576, incorporated herein by reference). Indeed, analysis of the structure of the putative HLA-DM molecule by sequence alignment with HLA-DR1 predicts with only moderate confidence that HLA-DM folds to form a peptide binding cleft.

Of the five residues in the α1 domain that are conserved throughout HLA class I and class II sequences, four are found in HLA-DM; however, DM shares only three of ten conserved (class I and class II) residues in the β1 domain, and alignment of DMβ with other class II β chains places a number of insertions and deletions in the β1 helix (Kelly, et al., supra; Cho, et al., supra, Brown, et al., *Nature* (1993) 364:33–39, incorporated herein by reference, and J. Brown, personal communication). Additionally, unlike other class II molecules, the β1 domain shows limited polymorphism in the mouse.

β1 contains seven cysteine residues, five of which are in novel positions (2 in the a chain and 3 in the β chain). A predicted structure for the folded DM molecule, based on its structural homology to other MHC molecules, suggests possible formation of two disulfide bonds in addition to the conserved bond found in the membrane distal domain of class II β chains. The DM molecule may thus have a more rigid structure than orthodox class II molecules (J. Brown, personal communication).

The failure of the DMB mutants to generate the normal repertoire of MHC class II/peptide complexes suggests several models for DM function. DM could act as a class II chaperon, mediating either a trafficking step or a folding event necessary for intracellular peptide binding. If HLA-DM assumes a class II-like structure, however, other possibilities may be more likely. DM may act as a peptide shuttle to deliver peptides to a compartment for association with conventional class II molecules. In this scenario, peptide binding to DM would constitute an initial step in determinant selection for class II binding peptides, and the association of class II molecules with Ii fragments in the mutants would reflect decreased availability of other peptides. Alternatively, the DM molecule may be required for optimal removal of the Ii peptides (amino acids 80–103). According to this model, the peptide binding groove of DM will have evolved to bind these Ii peptides with high efficiency, thereby favoring binding of immunogenic peptides to other class II molecules. The existence of a DM as a "sink" for Ii peptide would accomplish Ii removal without the use of peptidases in a compartment where immunogenic peptides likely reside as well.

In the foregoing models, HLA-DM, like other class II molecules, may be a peptide binding molecule, but with a function that differs fundamentally from that of other class II molecules: the peptide/DM complex may not be a ligand for T cells and its critical role may be an intracellular one. The lack of homology to other class II β chains in the conserved region of the membrane proximal (β2) domain, which mediates interaction with the CD4 coreceptor (Cammarota, et al., *Nature* (1992) 356:799–801 and Konig, et al., *Nature* (1992) 356:796–798, both incorporated herein by reference), is consistent with this model. In addition, mice that lack expression of I-A and I-E molecules, but have normal Ma and Mb genes, show near complete depletion of mature CD4+ T cells, further suggesting that Ma/Mb does not function as an element for positive selection of T cells in the thymus (Cosgrove, et al., *Cell* (1991) 66:1051–1066 and Grusby, et al., *Science* (1991) 253:1417–1720, both incorporated herein by reference).

Consistent with the possibility that DM functions at an intracellular site, the DMβ and Mb sequences also diverge from class II β chains at three of four positions within a highly conserved region (amino acids 80–83) that has been implicated in transport and targeting of class II molecules to the cell surface (Griffith, et al., *J. Exp. Med.* (1988) 167:541–555 and Sant, et al., *Hum. Immun.* (1993) 37s:3, both incorporated herein by reference). In both DMβ and Mb, threonine is substituted for a conserved asparagine in this region (position 82N in I-Aβ); a very similar substitution (serine for asparagine) in mutant I-A β chains results in intracellular retention of sialyated, mutant I-A molecules (Griffith, et al, supra).

Interestingly, a DRA point mutant has been isolated in which aberrant glycoslylation in the second domain of HLA-DRα results in association of the mutant DR molecules with Ii peptides (amino acids 80–103) (Mellins, et al., *J. Exp. Med.* (1994) 179:541–549.) As both mutation of DRA and DMB generate HLA-DR molecules with similar characteristics, one attractive hypothesis is that direct association between class II molecules and DM molecules is required for DM function. Consistent with this hypothesis, homotypic interaction between HLA-DR1 molecules has been shown to occur during crystallization, and the resulting dimer or dimers includes an interface near the region altered in the mutant DR molecules (Brown, et al. supra).

Figure 12:
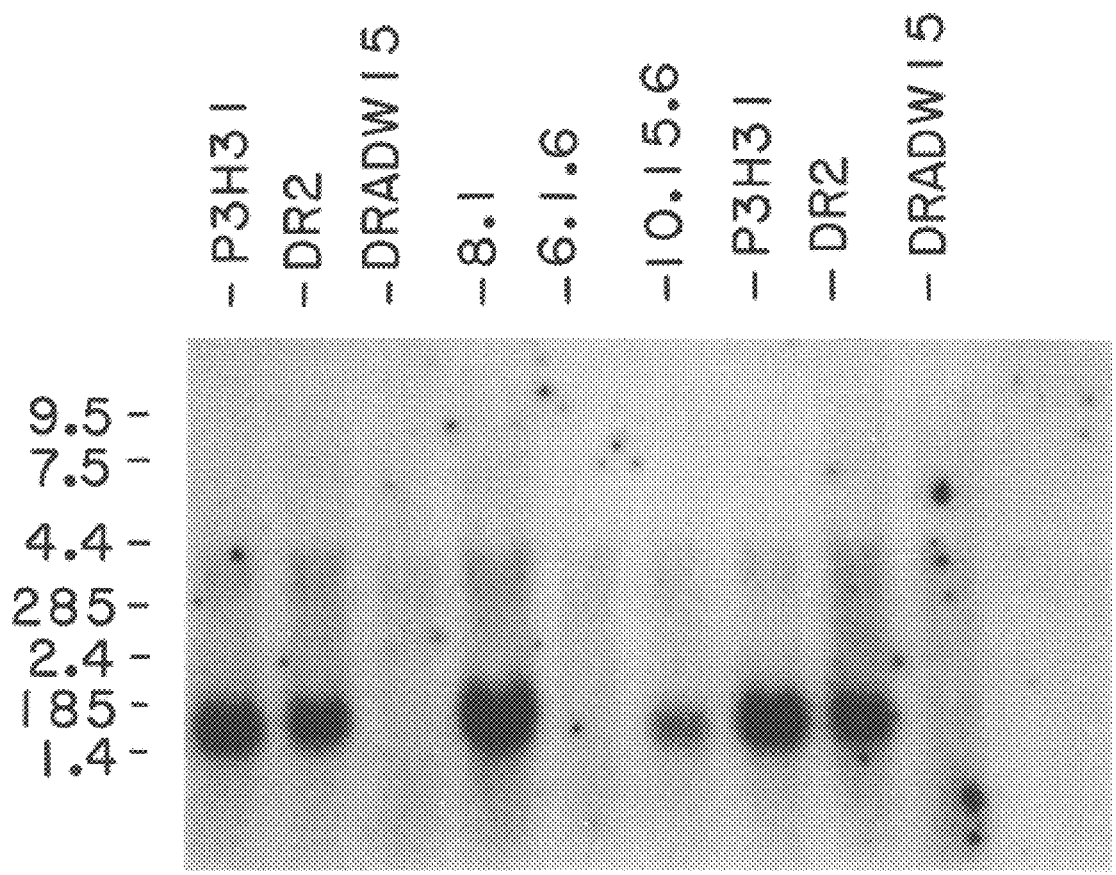
FIG. 12 depicts Northern blot analyses of cellular extracts probed with DMB cDNA.

MHC class II/peptide association is significantly modulated by the level of expression of HLA-DM. Further, the expression of DM and other class II molecules has been shown to be coregulated. (Kelly et al., supra, and unpublished results.) Kelly et al., supra, reported that DR and DM are coordinately induced by γ interferon. This coregulated expression and coordinate induction likely promote presentation of non-self peptides by activated antigen presenting cells. Conversely, lack of DM expression favors presentation of a limited range of peptides. In addition, DMβ expression is reduced in B cells obtained from a patient with bare lymphocyte syndrome, an immunodeficiency syndrome resulting from a lack of transcription factors required for expression of conventional MHC class II molecules, i.e. DR. (FIG. 12)

One implication of the foregoing is that of diagnosing and treating immunocompromised patients wherein the etiological origin is not related specifically or solely to another causative factor. A mutant DMB product, or lack thereof as a result of a mutation in the HLA-DMB locus, could result in a defect in the presentation of antigen and, therefore, an immunocompromised presentation. Treatment could involve the administration of wild-type HLA-DMB nucleic acid, either in the form of DNA—cDNA and genomic—or mRNA.

However, the involvement of DMβ in antigen presentation also presents possibilities for treatment of autoimmune diseases. Essentially, an autoimmune disease state arises upon lack of tolerance for self. Consequently, the identification of the role of DMβ in presentation of antigen suggests opportunities for treating autoimmune disorders. Such disorders contemplated include diabetes mellitus, chronic dermatitis, rheumatoid arthritis, multiple sclerosis, myasthenia gravis, and systemic lupus erythematosus to list just a few. More comprehensive lists can be found in any medical immunology text.

Naturally, the course of treatment for autoimmune diseases will depend, to some extent, upon the identification of the precise function of DMβ in antigen presentation. For example, the function could occur completely intracellularly, or it may involve extracellular aspects. In the case of the latter, antibodies directed against DMβ can be utilized.

Regardless of whether the function is intra- or extracellular, treatment resulting in the inhibition of function of DMβ in the specific tissue affected is desirable. It is assumed that such treatment would likely result in the inactivition of the complete DM molecule as well, since it is likely that DMα and DMβ form a dimer.

In the case of extracellular function, specificity can be bestowed by antibody recognition. In the case of intracellular function, specificity will depend upon other means. For example, in the case of chronic arthritis, specificity can be effected by locale, such as through intraarticular administration of a therapeutic agent.

For autoimmune diseases affecting internal organs, some other mechanism for conferring specificity is necessary. For example, a gene construct producing antisense message driven by an organ specific promoter can be utilized. In the specific case of diabetes mellitus, an insulin promoter can be utilized. Organ specific expression of transgenes is reported upon in Oldstone et al., *Cell* (1991) 65:319–331 (incorporated herein by reference).

The agent for inhibiting the function of DMβ can also be an antisense oligonucleotide directed against HLA-DMB mRNA. For example, see Calabretta et al., *Cancer Treatment Reviews* (1993) 19:169–179; Gewirtz, A. M., *Leukemia and Lymphoma* (1993) 11:131–137; and Ratajczak et al., *Proc. Nat. Acad. Sci. USA* (1992) 89:11823–27 (all incorporated herein by reference). Alternatively, small molecules which inhibit the function of DMβ, i.e. peptides which bind to DMβ, can also be utilized. In the event antisense oligonucleotides are utilized, the oligonucleotides can be modified for increasing stability and cellular uptake, as has been disclosed in the literature. In that regard, the phosphorothioate forms of the oligonucleotides can be utilized. Further, in the case of both the oligonucleotides and small molecules, a carrier can be utilized. The carrier can be used to confer specificity on the oligonucleotide or molecule. Examples of such carriers are liposomes—in particular, liposomes with antibodies, or their antigen binding fragments, incorporated therein.

In addition to the therapeutic uses outlined above, the agent inhibiting the function of DMβ can also be used in in vitro applications. One such application is the determination whether an added or synergistic effect results if the expression of another participant in antigen presentation is concurrently suppressed. A cell-based system such as described below in T-cell proliferation assays can be utilized in this application.

An additional in vitro application involves a test for determining the role of antigen presentation in the etiology of autoimmune diseases. The precise mechanism of disease for many diseases which have been catergorized as "autoimmune" has not yet been elucidated. However, several steps in the pathophysiologies have been identified. For example, it has been established that the production of collagenase and interleukin- 1 (IL1) each represent one step in the pathophysiology of rheumatoid arthritis. (Harris, E. D., "Mechanisms of Disease", *New Eng. Jour. Med.* (1990) 322:1277–1289, incorporated herein by reference.) Consequently, an in vitro assay which detects changes in production of either of these compounds in a culture of synovial cells from a patient with rheumatoid arthritis, upon addition of the agent inhibiting the function of DMβ, would suggest a relationship.

Since, as determined by the present inventor, DMβ clearly plays a critical role in antigen presentation, it is further contemplated that modulation of DMβ function will find application in other situations in which the modulation of antigen presentation is desirous. Three such situations include vaccine development, tumor therapy, and organ transplantation. For vaccine development and tumor therapy, the stimulation of a specific immune response is desirous. Contrastingly, for organ transplantation, it is the suppression of a specific immune response which is desirous. Modulation of DMβ function could afford mechanisms to achieve both of these goals.

MATERIALS AND METHODS

Derivation of Cell Lines

Cell lines 8.1.6, 9.5.3 and 5.2.4 were derived from B-lymphoblastoid cell line T5-1. FIGS. 1 and 2 depict the derivation and mapping of deletion breakpoints in 8.1.6. Deletion is shown as hatched boxes. T5-1 is an EBVtransformed B cell line. 8.1.6 was derived directly from T5-1 by ethyl methane sulfonate (EMS) mutagenesis of T5-1 and selection with an HLA-DR1 antiserum and complement (C'), as described (Gladstone, et al., *Nature* (1978) 271:459–461, incorporated herein by reference.) Mutant 9.5.3 was derived from 8.1.6 by EMS mutagenesis of 8.1.6 and selection with monoclonal antibody (mAb) 16.23 and C' (Pious, et al., *J. Exp. Med.* (1985) 162:1193–1207, incorporated herein by reference); mAb 16.23 recognizes a polymorphic determinant on DR3β1 molecules and some DRβ3 specificities. Mutant 5.2.4 was isolated from 8.1.6 after EMS mutagenesis of 8.1.6 and selection with a monomorphic anti-DR antibody, VI.15, and C' (Mellins, et al., (1991), supra). The phenotypic characterizations of mutants 9.5.3 and 5.2.4 have been described previously. (Mellins, et al., (1990) and Mellins, et al., (1991), respectively).

Southern Blot Analysis of 8.1.6

Genomic DNA (10–20 µg/lane) was digested to completion with PflM I, separated on a 0.7% agarose gel, transferred to Zeta probe GT membrane (Bio-Rad) and hybridized with various $^{32}$P-labelled DNA probes, according to manufacturer's guidelines. The results are depicted in FIGS. 3a–3c. The DMB-5' probe used was a 235 bp fragment amplified from the 5' untranslated portion of the HLA-DMB gene by PCR (5' primer:
5' CCTGTTTGGGACACTGACTC 3' (SEQ ID NO:1); 3' (anti-sense) primer: 5' ATGCTCTGCTCTGTAAAGATG 3' (SEQ ID NO:2). This fragment was amplified from 8.1.6 genomic DNA, but can also be amplified from CDNA from 8.1.6, thereby indicating a different transcription start site in 8.1.6 than previously reported in Kelly, et al., supra. The DMB-3' probe is a 151 bp fragment amplified from the 3' untranslated portion of the DMB gene by PCR (5' primer: 5' TCCCCTATGTAAAACTTAGCA 3' (SEQ ID NO:3); 3' (anti-sense) primer: 5' GTCCTCTATGGCACACTGAGA 3' (SEQ ID NO:4) (Kelly, et al. supra). A full length DRA cDNA probe was kindly provided by Dr. Ming-der Chang, North Shore University Hospital, Manhasset, N.Y. The sequence of DRA cDNA is reported in Marsh et al., *Human Immunology* (1992) 35:1–17, incorporated herein by reference.

In FIG. 3a, the single band from T5-1 that hybridizes with the DMB-5' probe indicates that the PflM I sites are conserved in the DR3 and DR1 haplotypes of the diploid cell, T5-1; the MHC deletion on the DR1 haplotype in 8.1.6 generates a restriction fragment length polymorphism (RFLP) detected by the DMB-5' probe.

Northern Blot Analysis of Mutants

Total cellular RNA (generally 20 µg/lane) was prepared by the guanidinium thiocyanate method of Xie, et al., *Bio Techniques*, (1991) 11:325–327 (incorporated herein by reference), fractioned by electrophoresis in agaroseformaldehyde gels, and transferred to Zeta Probe GT (Bio-Rad) membranes. The blots were hybridized according to manufacturer's guidelines with a full length DMB cDNA (Kelly, et al., supra), and then stripped and re-probed with a 540 bp fragment amplified from the β-actin gene (5' primer: 5' GTGGGGCGCCCCAGGCACCA 3' (SEQ ID NO:5); 3' (anti-sense) primer: 5' CTCCTTAATGTCACGCAC-GATTTC 3' (SEQ ID NO:6); primers were provided by Dr. Elwin Loh, University of Pennsylvania, Philadelphia, Pa. Autoradiography was continued for 7 days with DMB probe and 4 hours with β-actin probe.

Figure 4:
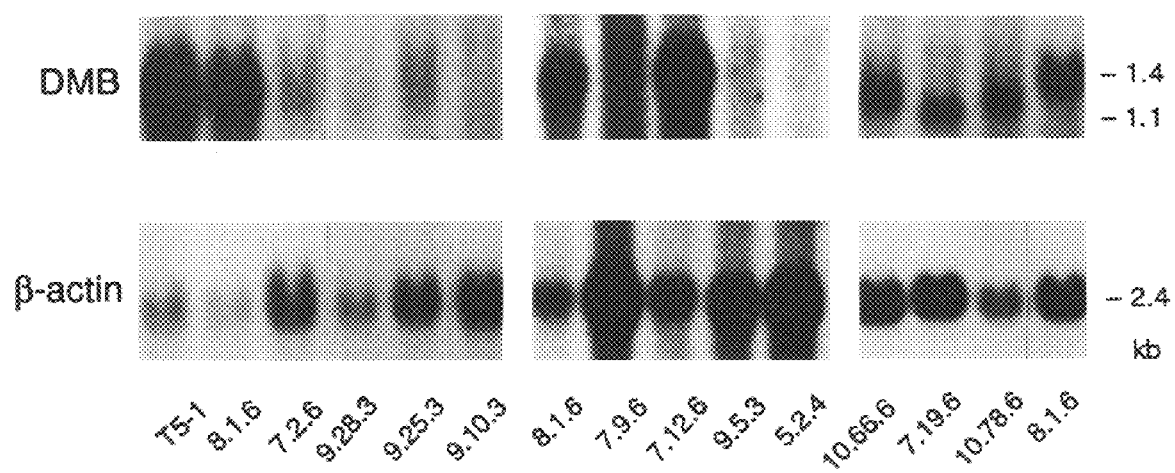
FIG. 4 depicts Northern blot analyses probed with DMB cDNA and β-actin, respectively.

The results of Northern blot hybridization of RNA samples from B-LCLs T5-1, 8.1.6, and class II presentation defective mutants 7.2.6, 9.28.3, 9.25.3, 9.10.3, 7.9.6, 7.12.6, 9.5.3, 5.2.4, 10.66.6, 7.19.6, and 10.78.6 with DMB cDNA (upper) and β-actin (lower) probes are depicted in FIG. 4. A decreased amount of T5-1 and 8.1.6 RNA was loaded on the left blot, which further highlights the reduction in DMB RNA in mutants. Mutants 7.12.6, 9.10.3, and 9.28.3 were isolated by the same immunoselection protocol as mutant 9.5.3 (FIG. 1). The DMB transcript was reduced in amount, but was of normal size in both mutant 9.10.3 and mutant 9.28.3 (FIG. 4).

Determination of Epitope Expression of Mutants

Figure 5:
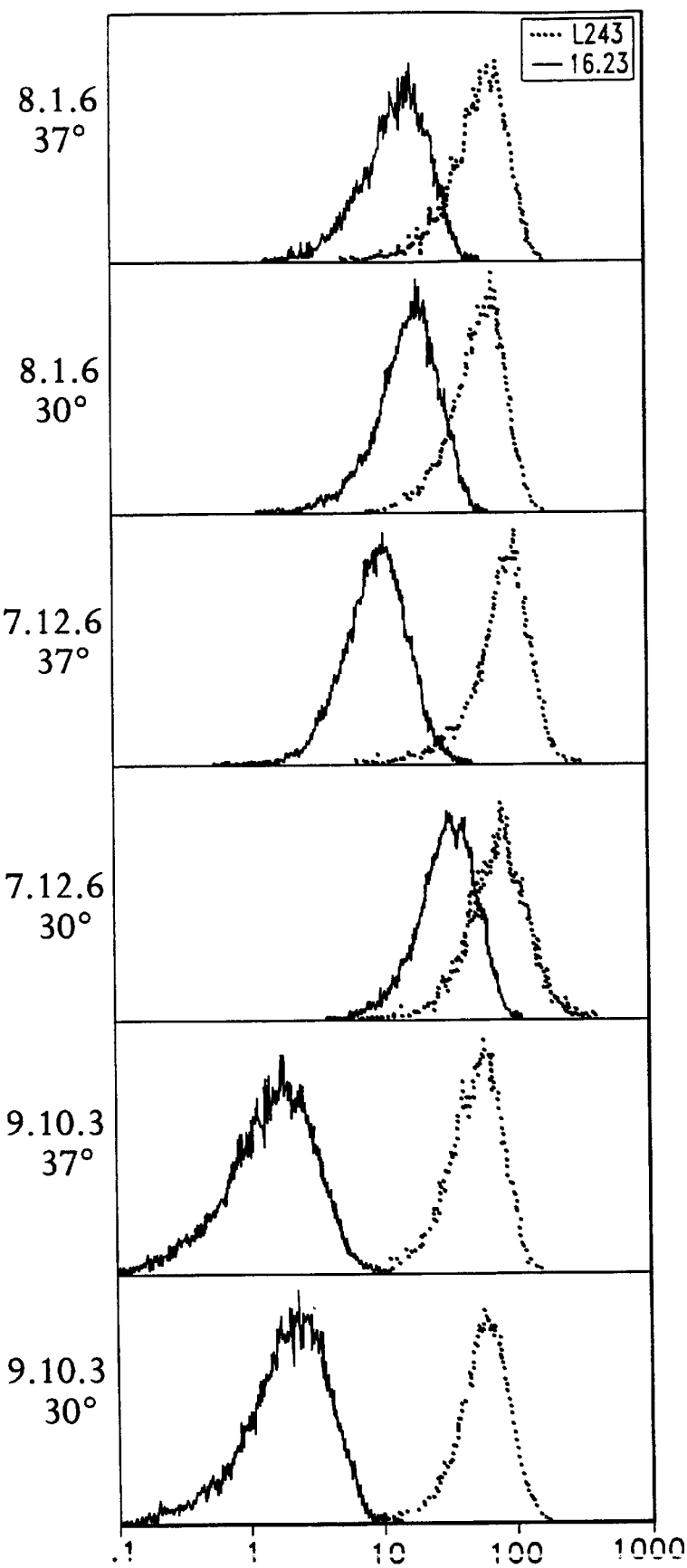
FIGS. 5A–5F depict binding of mutants to monoclonal antibody 16.23 and antibody L243.

For temperature shifted cells, cells were grown at 30° C. for 7 days prior to assay; an increase in binding of mAb 16.23 to 7.12.6 cells was observed after 48 hour culture at low temperature and was maximal by 4 days (unpublished results). For fluorescence activated cell sorter (FACS) analysis, cells were incubated with saturating amounts of unlabelled primary antibody, followed by saturating amounts of fluoresceinated goat anti-mouse IgG (H+L) (Gibco-BRL). In all assays, binding of fluorescein isothiocyanate (FITC)-labelled goat anti-mouse antibody alone was used as a control. Indirect immunofluorescent analysis was carried out using the following antibodies: anti-DR3 (solid lines): 16.23 (Johnson, et al., *J. Exp. Med.* (1982) 156:104–111, incorporated herein by reference); anti-DR dimer (dotted lines): L243 (Lampson, et al., *J. Immun.* (1980) 125:293–299, incorporated herein by reference). Binding of flouresceinated goat anti-mouse antibody alone is shown for 8.1.6 in FIGS. 9A–9G; comparable staining with control antibody was observed with all cell lines (not shown). Stained cells were analyzed on a EPICS Elite (Coulter). Cell number is displayed against a 4 log unit axis of fluorescence intensity (FIGS. 5 and 9).

The results presented in FIGS. 5A–5F indicate that mutant 7.12.6 has a milder, temperature sensitive phenotype which was determined to be associated with a point mutation in the DMB gene. Mutant 7.12.6 binds mAb 16.23 at higher levels than class II presentation defective mutant 9.10.3; the binding of mAb 16.23 to 7.12.6, but not 9.10.3 cells, is increased by cell culture at 30° C. The 7.12.6 cell surface expression of HLA-DR, as detected by binding of monomorphic anti-DR antibody L243, was slightly higher than that of progenitor 8.1.6. The binding of L243 to both 8.1.6 and 7.12.6 was slightly diminished by culture at low temperature.

Stability of Mutant Dimers

Figure 6:
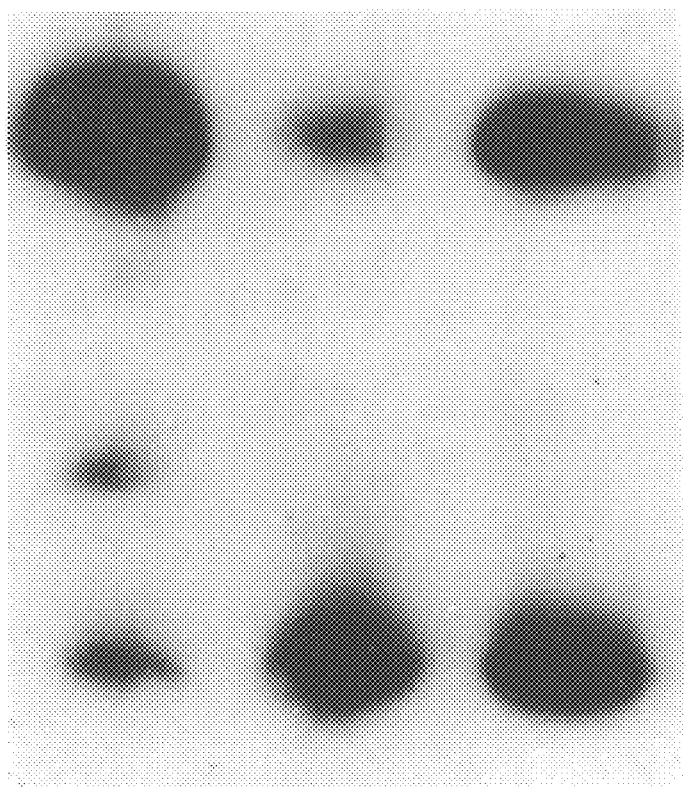
FIG. 6 depicts the stability of DR dimers from mutants 9.10.3 and 7.12.6 in SDS detergent solution as determined by immunoblotting.

Western blot analyses were carried out essentially as described by Pious, et al., except that polyvinylidene difluoride (PVDF) membranes were used and bands were developed with enhanced chemiluminescent reagents (Gibco-BRL). Results are depicted in FIG. 6.

HLA-DR (FIG. 6) and -DP (data not shown) dimers extracted from mutant 7.12.6 are more stable in SDS detergent solution than dimers from mutants 9.10.3, but less stable than dimers from progenitor 8.1.6. Unboiled, whole cell NP-40 extracts were analyzed by 1-D SDS-PAGE and immunoblots were developed with HB10.A (anti-DRβ antibody) (Clark, et al., *Leukocyte Typing* (1984) (eds. Bernard, A., Baunsell, L., Dausset, J. and Schlossman, S.) 195 (Springer, Heidelberg)).

Stimulation T Cell Proliferation

Stimulation of proliferation HLA class II restricted T cells using mutants 7.12.6 and 9.10.3 and progenitor 8.1.6 as APC was tested. The isolation of antigen specific T cells has been described elsewhere. Mellins, et al., (1990), supra, and Mellins, et al., Hum. Immun. (1987) 18:211–223 (incorporated herein by reference).

The alloreactive, anti DR3 clone was isolated as described in Johnson, et al., ImmunoBiology of HLA (ed. Dupont, B.O.) (Springer, New York, 1984) and was the gift of Dr. Armead Johnson, Georgetown University, Washington, D.C. For assay, $2 \times 10^4$ cell blasts were co-cultured with $1–1.5 \times 10^5$ mitomycin-C treated B-LCLs as APC or stimulators. For antigen specific T cells, assays were performed in the presence or absence of native antigen—purified protein derivative of M. tuberculosis (PPD) or tetanus toxoid (TT)—at 10 or 15 $\mu g$ $ml^{-1}$, respectively. To measure T cell proliferation, cultures were pulsed with 1 $\mu Ci$ of [$^3$H] thymidine for the last 12 hours of a 60 hour culture. The polyclonal, class II restricted T cell lines utilized are designated by antigen (PPD or TT). T cells with the same apparent specificity were derived from separate donors.

Specific T cell stimulation was measured as [$^3$H] thymidine incorporation: (c.p.m. in the presence of antigen-c.p.m. in the absence of antigen or, for alloreactivity, c.p.m. in the presence of stimulators-c.p.m. in the absence of stimulators). Results are presented in FIG. 7 and are expressed as percent stimulation of that observed with progenitor 8.1.6 as APC and are median values from triplicate cultures from a representative experiment; similar results were obtained in three or more independent experiments. Stimulation of T cells with 8.1.6 as APC: PPD/class II, 6564 c.p.m.; TT/class II, 14011 c.p.m.; TT/class II, 8953 c.p.m.; Allo/DR3, 17049.

Sequence Analysis

Figure 13A:
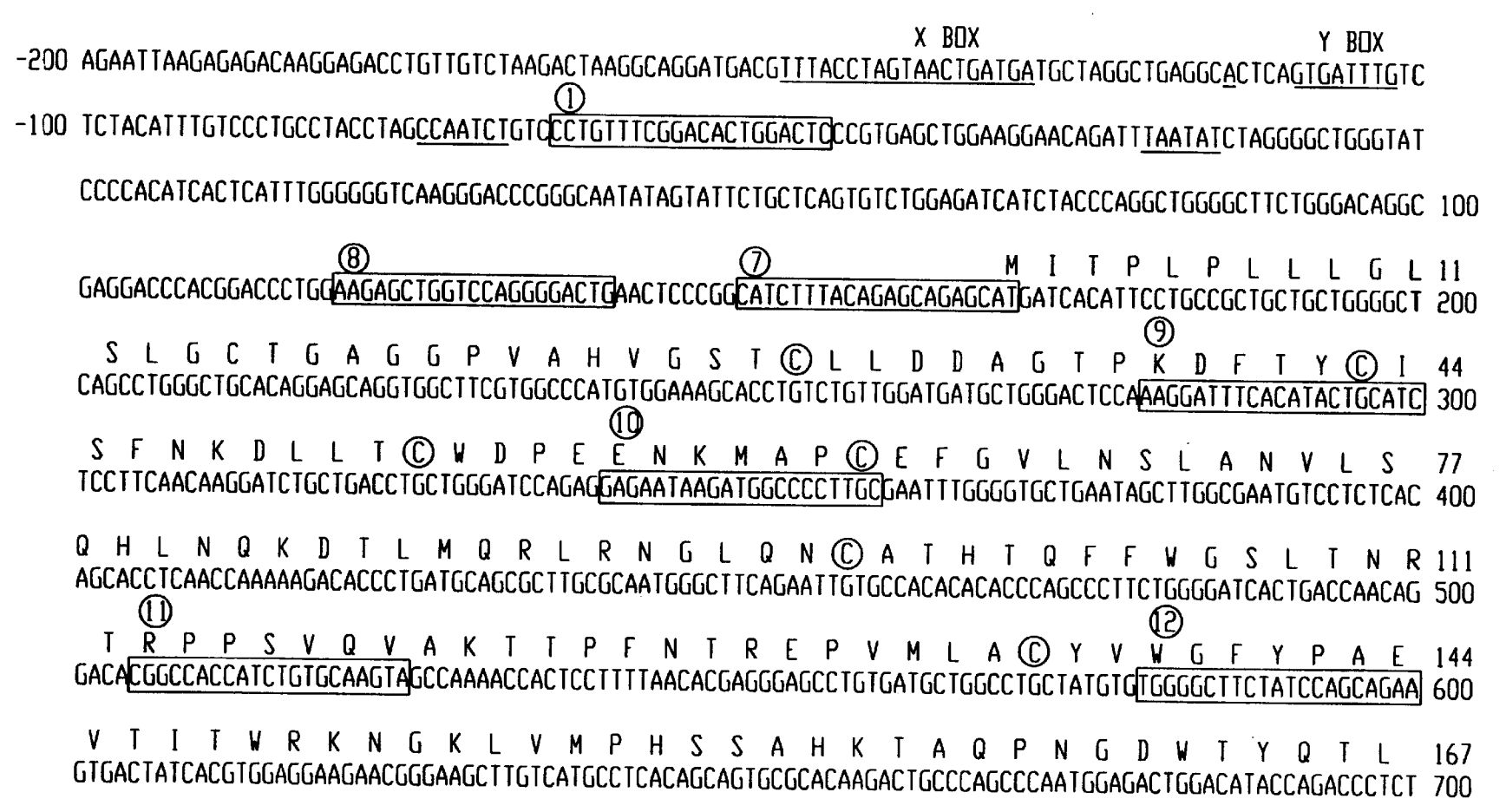

Total cellular RNA was prepared from mutant 7.12.6 and progenitor 8.1.6 by the guanidinium/thiocyanate method of Xie, et al., BioTechniques (1991) 11:325–327, incorporated herein by reference. Five $\mu g$ of each RNA preparation was reverse transcribed using Moloney murine leukemia virus reverse transcriptase and priming with the 3' (anti-sense) primer of the DMB-3' primer pair (SEQ ID NO: 4) to yield cDNA corresponding to the DMB gene of the DR3 haplotype (FIG. 1). After ethanol precipitation and resuspension, the cDNA/RNA was amplified using primer pairs selected to amplify 200–400 base pair overlapping segments of the DMB coding region. Primers were developed with the assistance of Dr. Ming-Der Chang of Northshore University Hospital. The primers utilized are presented in Table I below and their locations on the HLA-DMB sequence as reported by Kelly et al., supra, are depicted in FIGS. 13A–13B. In FIGS. 13A–13B, the primers are enclosed in boxes. The respective SEQ ID NO:'s are circled. In Table I, all sequences are reported in the 5' to 3' direction. Anti-sense sequences are so indicated.

TABLE I

| PRIMER DESIGNATION | SEQUENCE 5'————→4' | SENSE | SEQ ID NO: |
|---|---|---|---|
| DMβ$_1$ 5' | CCTGTTTGGG ACACTGGACT C | sense (S) | 1 |
| DMβ$_1$ 3' | ATGCTCTGCT CTGTAAAGAT G | antisense (A) | 7 |
| MC107 | AAGAGCTGGT CCAGGGGACT G | S | 8 |
| MC114 | GATGCAGTAT GTGAAATCCT T | AS | 9 |

TABLE I-continued

| PRIMER DESIGNATION | SEQUENCE 5'————→4' | SENSE | SEQ ID NO: |
|---|---|---|---|
| MC108 | GAGAATAAGA TGGCCCCTTG C | S | 10 |
| MC113 | TACTTGCACA GATGGTGGCC G | AS | 11 |
| MC109 | TGGGGCTTCT ATCCAGCAGA A | S | 12 |
| MC112 | AATGTGCTCT ACCACACAGG T | AS | 13 |
| DMβ 9415' | CTGTGTGGTA GAGCACATTG G | S | 14 |
| MC110 | TCGGGACTGG ACACCTGGGC T | S | 15 |
| DMβ 9983' | AGGGTCTGCA TGGGGGACAG C | AS | 16 |
| DMβ 10963' | GAGTGTAACT AGAGTGGCCA G | AS | 17 |
| DMβ 11103' | GGACCCAGGA AGAGGAGTGT | AS | 18 |
| MC111 | AGAGGCATGG TAGCATCATT G | AS | 19 |
| DMβ$_2$ 5' | TCCCCTATGT AAAACTTAGC A | S | 20 |
| DMβ$_2$ 3' | GTCCTCTATG GCACACTGAG A | AS | 21 |

PCR was performed in an Idaho Technology Air Thermo-Cycler for 40 cycles (94° C. for 25 seconds, 50–54° C. for 30 seconds, as appropriate for particular primers, and 72° C. for 33 seconds). PCR products were subjected to gel electrophoresis and appropriate bands were recovered using the QIAEX Gel Extraction Kit (Qiagen, Inc.) per manufacturer's protocol. Amplified cDNA fragments were sequenced directly using cycle sequencing (Cyclist II, Stratagene); 250 $\mu g$ of bovine serum albumin was added to each sequencing reaction as is standard for capillary PCR reactions. Cycle sequencing was performed on the Air Thermo-Cycler for 40 cycles (94° C. for 5 seconds, 50–54° C. for 15 seconds, and 72° C. for 20 seconds). The 7.12.6 mutation was sequenced on both strands (data not shown).

EXAMPLES

Example 1

Mapping the Genetic Lesion in the Mutants

Sixteen independent B-LCL mutants with the presentation-defective phenotype (e.g. 9.5.3) were derived from an HLA-DR/DQ hemizygous 8.1.6 by replicate immunoselection experiments with a DR3-specific monoclonal antibody, 16.23 (FIG. 1; Mellins, et al., (1990), supra, and Pious, et al., (1985), supra); the related mutant, 5.2.4, was also derived from 8.1.6 by selection with a monomorphic anti-DR antibody, VI.15 (FIG. 1; Mellins et al., (1991), supra, and Gladstone, et al., (1982), supra. Analysis with 5.2.4 (Mellins, et al., (1991), supra and additional MHC deletion mutants (Ceman, et al., (1992), supra) placed the gene(s) responsible for the phenotype within the centromeric ~230 kb of the region deleted in progenitor 8.1.6. To further refine the mapping of this gene, the centromeric breakpoint of the 8.1.6 deletion was established. As shown in FIGS. 3a–c, a 200 bp fragment of the 5' untranslated region of the DMB gene (DMB-5') is present on two PflM I restriction fragments in 8.1.6 genomic DNA. Comparison with the band pattern observed in the related cell lines, T5-1 and 5.2.4, allowed assignment of the PflM I fragments to the two MHC haplotypes of progenitor 8.1.6 (14.1 kb fragment: DR3 haplotype; 13 kb fragment: DR1 haplotype). A 185 bp fragment from the 3' untranslated region of DMB (DMB-3')

is found only on the 14.1 kb fragment and is therefore present only on the DR3 haplotype. These findings located the centromeric breakpoint of the 8.1.6 deletion within the DMB gene of the DR1 haplotype; this mapping was confirmed by PCR amplification of segments of the DMB coding region (data not shown).

The telomeric breakpoint of the 8.1.6 deletion lies within the first exon of the DRA gene (data not shown); as a result, a segment of DRA is also found on the 13 kb PflM I fragment in 8.1.6 and its derivatives, 5.2.4 and 9.5.3 (FIG. 3c).

Example 2
Evaluation of DMB Gene in the Mutants

The disruption of one copy of the DMB gene in progenitor 8.1.6 with retained antigen presentation activity suggested that mutation of the remaining DMB gene (DR3 haplotype) was responsible for the class II presentation defect in 8.1.6-derived mutants. By Southern blot analysis with several restriction enzymes, no abnormality in the DR3-linked DMB gene in any of the mutants was detected except deletion mutant 5.2.4 (FIGS. 3a–c and data not shown). However, Northern blot analysis of DMB transcripts from the mutants revealed a striking number of abnormalities (FIG. 4). No DMB message is detectable in mutant 5.2.4, indicating that the truncated DMB gene of the DR1 haplotype in 8.1.6 (and its derivatives) does not produce stable transcripts. Northern analysis of DMB mRNA from the other mutants thus assesses the transcripts generated by the DR3-linked copy of the DMB gene.

The results are presented in FIG. 4. In 11 mutants, the DMB transcript is of normal size (1.4 kb), but is present in vastly reduced amounts; representative mutant cell lines, 7.2.6, 9.25.3, 9.28.3, 9.10.3, 7.9.6 and 9.5.3 are shown. In 3 mutants, the DMB transcript is moderately reduced in abundance and is of diminished length (~1.3 kb); mutants 10.66.6 and 10.78.6 of this type are shown. In a fourth mutant, 7.19.6, the length of the DMB RNA is only 1.1 kb. These results implicate DMB as the gene responsible for the mutant phenotype. Moreover, PCR amplification of complementary DMB DNA from those mutants with short transcripts indicates that each contains mutation within the DMB gene rather than truncation at the 3' end of the gene, these data argue strongly that mutation of DMB itself, not a closely linked gene, results in the class II presentation defect.

Example 3
Analysis of a DMB Point Mutant

One mutant, 7.12.6, expresses a DMB transcript of normal length and abundance (FIG. 4). The phenotype of this mutant is unique, although it was isolated in the same manner as the other mutants. The binding of the 16.23 mAb to mutant 7.12.6 is only moderately reduced (FIG. 5C) and a higher proportion of DR molecules from 7.12.6 maintain the dimeric state when extracted in SDS detergent (FIG. 6; compare 7.12.6 to 9.10.3). Moreover, when 7.12.6 cells are cultured at 30° C., the binding of the 16.23 antibody increases substantially (FIG. 5D), and dimer stability is enhanced (data not shown); this temperature sensitivity is not observed in any of the other sixteen mutants (e.g. 9.10.3, FIGS. 5E-5F).

Figure 7:
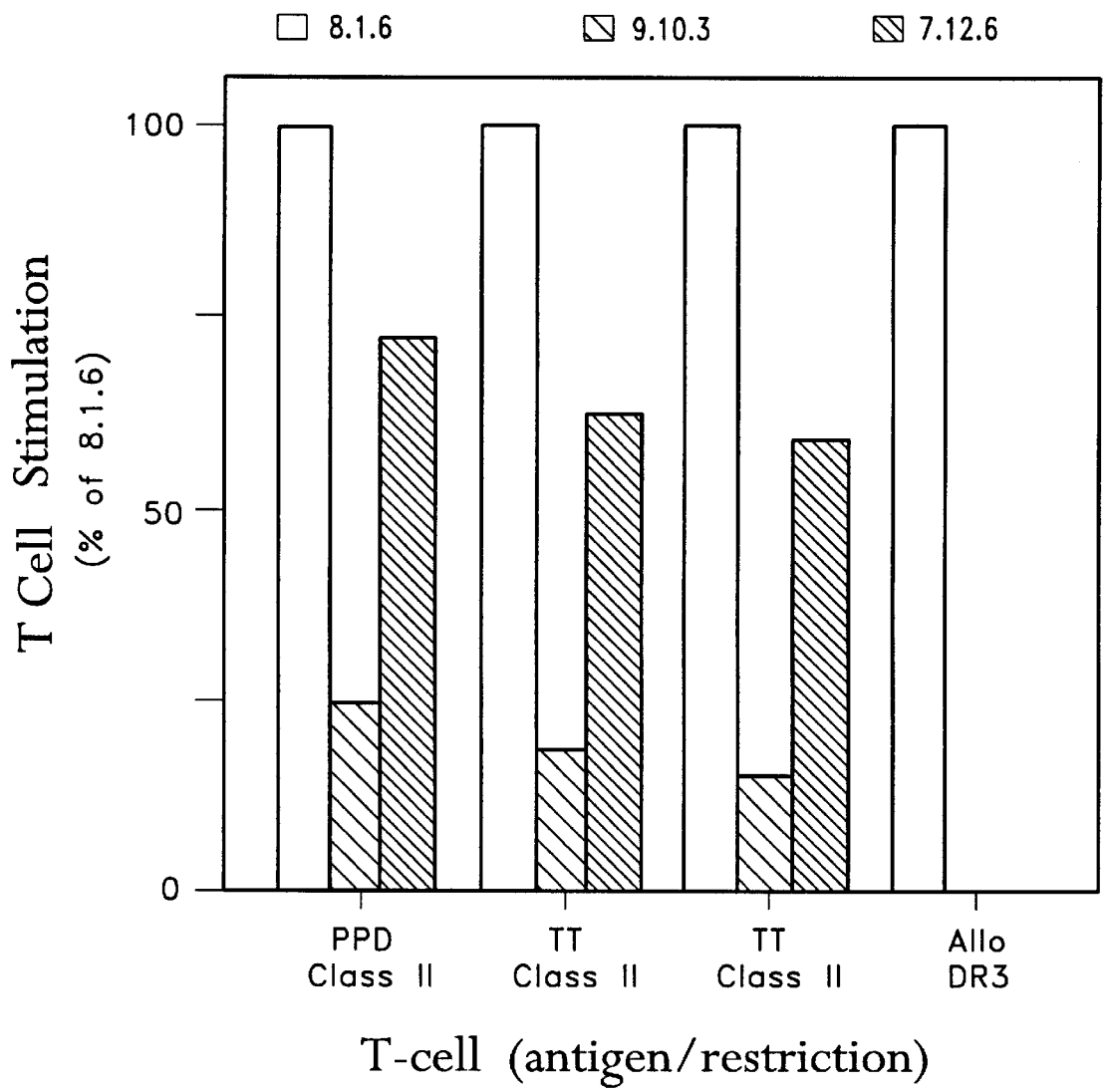
FIG. 7 depicts the proliferation of HLA class II restricted T cells by mutants using various antigens.

Assessment of T-cell reactivity to mutant 7.12.6 also reveals a milder defect compared to the other mutants: several antigen-specific polyclonal T-cell lines are moderately reactive to 7.12.6 cells plus native protein antigen (FIG. 7, see PPD-specific and tetanus toxoid-specific, class II restricted T cells), although certain individual T cell clones are nonresponsive to 7.12.6 cells as APC (FIG. 7, e.g., alloreactive anti-DR3 clone). Despite the milder phenotype of 7.12.6 cells, elution of peptides associated with affinity-purified HLA-DR molecules from 7.12.6 reveals a predominance of fragments of invariant chain (region 80–103), and a decrease in the fraction of the total peptide eluate accounted for by the Ii peptides in 7.12.6 was not detected (data not shown).

Figure 8:
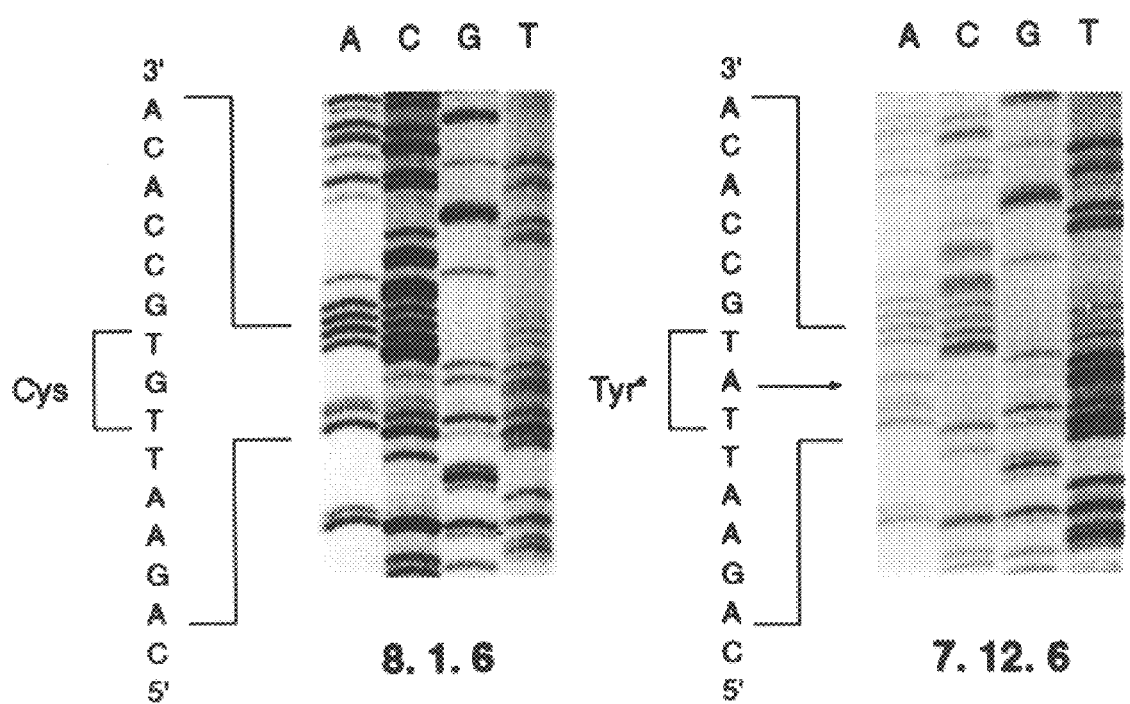
FIG. 8 depicts the sequence variation of the 7.12.6 point mutation.

To determine whether the 7.12.6 phenotype is associated with mutation of DMB, DMB cDNA from 7.12.6 was sequenced and compared to the sequence of DMB cDNA from progenitor 8.1.6. Sequence comparison of DMB cDNA from progenitor 8.1.6 and mutant 7.12.6 in the region of the 7.12.6 mutation is depicted in FIG. 8. The DMB sequence from mutant 7.12.6 is altered by a single base change (G→A), which results in a tyrosine for cysteine substitution at residue 79 in the putative membrane distal domain of the DMβ chain (FIG. 8). The mutated residue corresponds to a conserved cysteine which participates in an intrachain disulfide bond in MHC class I and class II peptide binding domains (See, Cho, et al., supra, and Kelly, et al., supra). No other coding region mutations were found in the DMB gene from 7.12.6. Thus, the findings from mutant 7.12.6 further support the conclusion that mutation of DMB underlies the class II presentation-defective phenotype and also imply that normal DMβ function requires maintenance of conformation in the region of the 7.12.6 mutation.

Example 4
Complementation by DMB cDNA

The data from 17 independent cell lines strongly implicated mutation of DMB as the basis of the mutant phenotype. To test this possibility, complementary DMB DNA was introduced into several mutant cell lines exhibiting reduced levels of endogenous DMB mRNA and the transfectants were evaluated, i.e., 9.5.3-DMB, 7.9.6-DMB, 7.2.6-DMB, for restoration of the wild type phenotype.

A full length DMB cDNA clone, previously described (See Kelly, et al., supra), was inserted into the expression vector pcDNA I/NEO (Invitrogen) using flanking polylinker sites EcoRV and Xho I. Mutant LCLs were electroporated with ScaI linearized plasmid DNA plus sheared salmon sperm DNA as carrier at 250 V, 250 $\mu$F or 350 V, 960 $\mu$F using a Gene-pulser with capacitance extender (Bio-Rad). After 3–4 days, selection was initiated on 1–1.5 mg ml$^{-1}$ G418 (Gibco-BRL). In some cases, after 11 days of selection, cells were co-cultured with normal diploid human fibroblasts as feeder cells. A full length Mb cDNA clone, previously described (Cho, et al. supra), was inserted into pcDNA I/NEO as well and transfection of the mutants by electroporation was carried out using the methods described above. Indirect immunofluorescence was carried out as in FIGS. 5A–5F; staining with control antibody was approximately equivalent for all cells and is shown for progenitor 8.1.6 only. Western blot analyses were carried out as in FIG. 6. The isolation of the DP4-restricted, HBsAg specific T cells has been described. The alloreactive, anti-DP4 T cells were isolated as described and were kindly provided by Susan Masewicz, Fred Hutchinson Cancer Research Center, Seattle, Wash. Recombinant HBsAg was the gift of Merck, Sharp, and Dohme, West Point, Pa. and was used a 1 $\mu$g ml$^{-1}$. T cell proliferation was assayed as in FIG. 7.

The regaining of epitope expression is depicted in FIGS. 9A–9K. Transfectants 9.5.3-DMB and 7.9.6-DMB regained binding of the 16.23 mAb; transfectants 7.2.6-DMB and 7.2.6-Mb regained binding of 16.23 mAb to a lesser degree. Indirect immunofluorescent analysis was carried out using the following antibodies: Control (dotted lines): flouresceinated goat anti-mouse antibody alone; anti-DR3 (solid lines): 16.23 (Johnson, et al. (1982) supra); anti-DR dimer (dashed lines): L243 (Lampson, et al., supra). The levels of HLA-DR on the transfectants were equivalent to the levels on the non-transfected mutants. Control transfectants 7.9.6-C and 7.2.6-C maintained the mutant phenotype for mAb 16.23 binding.

Figure 10:
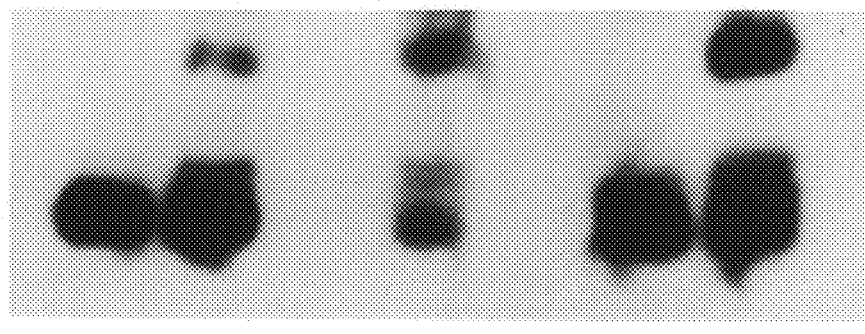
FIG. 10 depicts the regaining of stability of DR dimers from mutants 9.5.3 and 7.9.6 in SDS detergent solution after transfection.

HLA-DR dimers from transfectants 9.5.3-DMB and 7.9.6-DMB regained stability in SDS detergent solution. Results are depicted in FIG. 10. Unboiled, whole cell NP-40 extracts were analyzed by 1-D SDS-PAGE and immunoblotted with monoclonal antibody DA6.147, which recognizes DR dimer and DRα monomers. (Guy, et al., *Eur. J. Immun.* (1982) 12:942–948, incorporated herein by reference.) Previously, in both antigen presentation assays and dimer stability assays, HLA-DP molecules expressed by mutant 7.9.6 consistently showed a milder defect than either HLA-DR molecules of 7.9.6 or HLA-DP molecules of mutant 9.5.3. T cells are designated by restricting element and, where appropriate, by antigen; antigens were tetanus toxoid (TT) and hepatitis B surface antigen (HBsAg). T cell stimulation was measured as described above. Data are presented in FIG. 11 and are expressed as percent of stimulation observed with progenitor 8.1.6 as APC; stimulation by 8.1.6: TT/class II, 23108 c.p.m.; HBsAg/DP4, 19210 c.p.m.; Allo.DR3, 7030 c.p.m.; Allo/DP4 50690 c.p.m.

Figure 11:
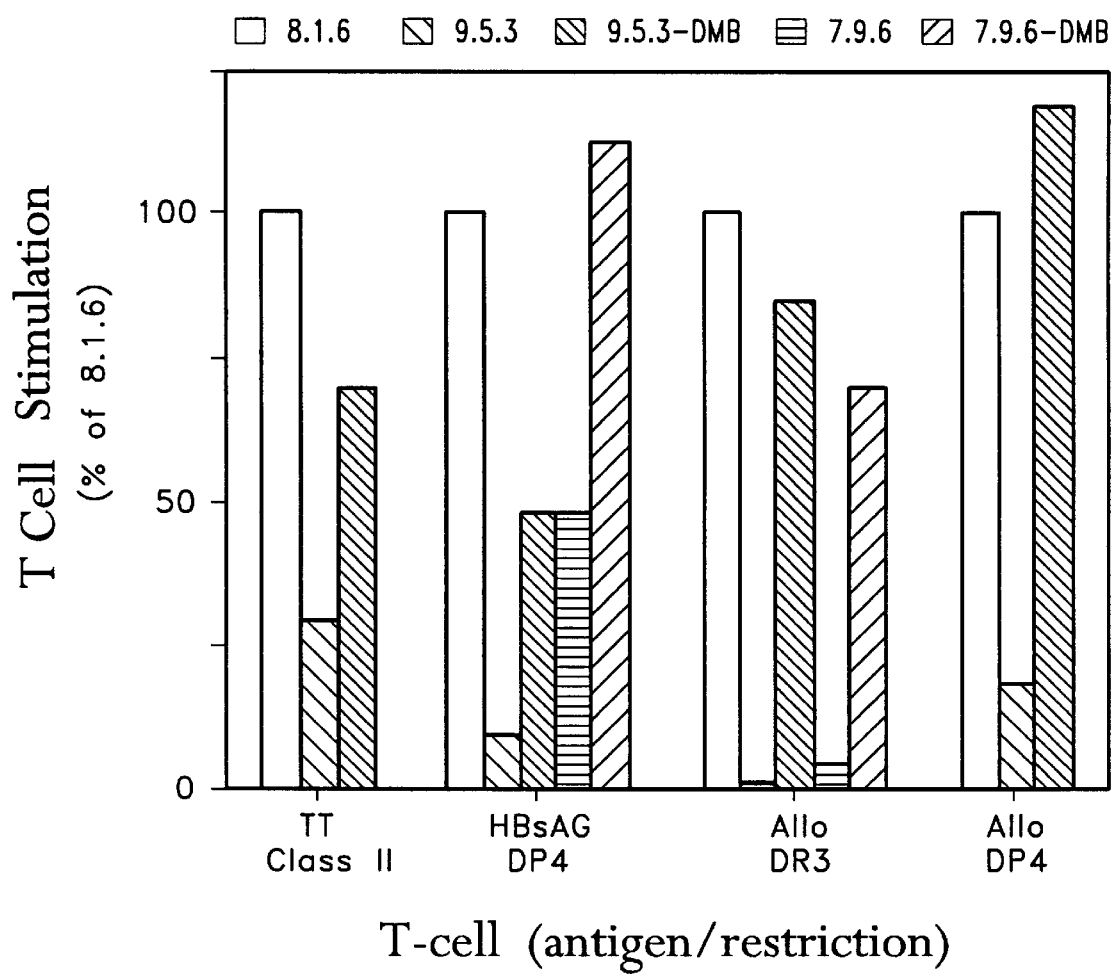
FIG. 11 depicts the proliferation of HLA class II restricted T cells by mutants and corresponding transfected mutants using various antigens.

As shown in FIGS. 9–11, the DR3 molecules expressed by the transfectants regained characteristics of DR3 molecules from wild type cells: they express the 16.23 epitope, which was lost in the mutants (FIGS. 9A–9K) and they demonstrate increased stability in SDS-PAGE (FIG. 10). Further, the DMB transfectants present native antigens to class II restricted T cells (FIG. 11) and stimulated alloreactive DR- and DP-specific T cells which do not recognize the mutants (FIG. 11). Transfection of the murine DMB homologue, Mb, also restores binding of the 16.23 antibody (7.2.6-Mb, FIG. 9J), whereas control cell lines transfected with the pcDNA/neo vector (7.9.6-C, 7.2.6-C) maintained the mutant phenotype (FIGS. 9F and 9K, respectively).

Example 5
Diagnosis of Mutation in Patients

Upon presentation of a patient exhibiting symptoms of unknown or unestablished etiological origin suggesting the patient is immunocompromised, a sample of B-lymphocytes from the patient can be collected, the nucleic acid extracted—either genomic DNA or mRNA—and analyses performed to determine whether the patient possesses a mutation in the HLA-DMB locus.

Specifically, the patient DNA can be isolated, PCR amplified as discussed previously, and tested for mutations using any available technique, such as single strand conformation polymorphism (SSCP) or RFLP. For example, see Example 2 and Orita et al., *Genomics* (1989) 5:874–879, incorporated herein by reference. The determination of a mutation in the HLA-DMB locus suggests the same as a causative factor in the disease state.

Alternatively, mRNA can be isolated from the patient cells and analyzed by Northern blot as described above and in Example 2. The complete absence of an HLA-DMB transcript can thus be determined.

In FIG. 12, mRNA was isolated from various cell lines and analyzed by Northern blot using a DMB cDNA as described previously. Cell lines designated P3HR1 and DRA-DW15 were isolated from patients exhibiting bare lymphocyte phenotype. Such patients are immunodeficient and, more specifically, are defective in the expression of numerous molecules important for immunological response, including class II molecules and invariant chain. DR2 indicates wild-type. Cell line 8.1.6 was described above. Cell lines 6.1.6 and 1015 are mutants generated in vitro. The second lane for P3HR1, DR2, and DRADW15 represents a repeat.

As shown in FIG. 12, the HLA-DMB transcript (1.4 kb) is absent from DRA-DW15 and the in vitro generated mutant cell line 6.1.6. Consequently, a mutational defect in HLA-DMB is indicated as one causative factor of immunodeficiency in patient sample DRA-DW15. Contrastingly, the presence of the HLA-DMB transcript in patient sample p3H R1 indicates that a mutational defect in HLA-DMB is not a causative factor in P3HR1.

Example 6
Method for Treating Immunocompromised Patients

Upon determination that a patient exhibiting an immunocompromised state harbors a mutation in HLA-DMB, gene therapy can be initiated to restore the defective function. A general, wide-based therapy can be initiated to restore wild type function or specific therapy targeted to bone marrow derived cells can be utilized. In this respect, ex vivo techniques of therapy are indicated.

Hematopoetic stem cells can be isolated from the patient, nucleic acid corresponding to the coding portion of wild-type HLA-DMB gene and an appropriate promoter—i.e, the autologous promoter—can be inserted into the cells using methods as described above in Example 4, and the transfected cells administered back to the patient. A review of the successful use of such techniques is provided in Miller, A. Dusty, *Nature* (1992) 357:455, incorporated herein by reference.

Example 7
Method for Treating Autoimmune Disease States

Upon determination that a patient is suffering from an autoimmune disease, localized treatment involving the inhibition of DMβ could be initiated. For example, in the event a patient is suffering from chronic arthritis, the target cells would be localized in the affected joint. Localization of the therapeutic agent is, thus, effected by the intraarticular administration of the treatment agent. The therapeutic agent can be an antisense oligonucleotide directed against the HLA-DMB mRNA, or some portion thereof, a small molecule that binds to DMβ, or a gene construct producing antisense message.

Example 8
Assay for Assessing Relationship of Antigen Presentation

Upon presentation of a patient with an autoimmune disease for which at least one measurable step in the pathophysiology has been established, a sample of the affected tissue is extracted. In the instance of rheumatoid arthritis, synovial cells are extracted from the joint. The affected tissue is then incubated under conditions reproducing the measurable pathophysiological step in vitro—i.e., production of collagenase for rheumatoid arthritis—and facilitating its measurement. An agent which inhibits the function of DMβ can then be added and any changes ascertained. In the specific case of rheumatoid arthritis, production of collagenase can be measured by measuring collagenase activity.

The foregoing examples are meant to illustrate the invention and not to limit the invention in any way. Those skilled in the art will recognize that modifications can be made which are within the spirit and scope of the invention as presented in the appended claims.

What is claimed is:

1. A method of determining in an immunocompromised patient that said patient is immunocompromised because of a defect in HLA-DMβ gene expression comprising:

a) isolating B lymphocytes from a patient assessed as being immunocompromised;

b) extracting nucleic acid from said B lymphocytes; and c) determining the expression level of the HLA-DMβ gene as compared to a normal control wherein a finding that HLA-DMβ expression is reduced or absent results in a determination that the patient is immunocompromised because of a defect in HLA-DMβ gene expression.

2. The method of claim 1 wherein said nucleic acid is messenger RNA.

3. The method of claim 2 wherein said messenger RNA is examined by Northern blot.

4. The method of claim 1 wherein said nucleic acid is genomic DNA.

5. The method of claim 4 wherein said nucleic acid is examined by Southern blot.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iv) ANTI-SENSE: NO (xi) SEQUENCE DESCRIPTION: SEQ ID NO:1:

CCTGTTTGGG ACACTGACTC                                                  20

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iv) ANTI-SENSE: YES (xi) SEQUENCE DESCRIPTION: SEQ ID NO:2:

ATGCTCTGCT CTGTAAAGAT G                                                21

(2) INFORMATION FOR SEQ ID NO:3:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iv) ANTI-SENSE: NO (xi) SEQUENCE DESCRIPTION: SEQ ID NO:3:

TCCCCTATGT AAAACTTAGC A                                                21

(2) INFORMATION FOR SEQ ID NO:4:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iv) ANTI-SENSE: YES (xi) SEQUENCE DESCRIPTION: SEQ ID NO:4:

GTCCTCTATG GCACACTGAG A                                                21

(2) INFORMATION FOR SEQ ID NO:5:

(i) SEQUENCE CHARACTERISTICS:
          (A) LENGTH: 20 base pairs (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:5:

GTGGGGCGCC CCAGGCACCA                                           20

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:6:

CTCCTTAATG TCACGCACGA TTTC                                      24

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:7:

ATGCTCTGCT CTGTAAAGAT G                                         21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:8:

AAGAGCTGGT CCAGGGGACT G                                         21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:9:

GATGCAGTAT GTGAAATCCT T                                         21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:10:

GAGAATAAGA TGGCCCCTTG C                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:11:

TACTTGCACA GATGGTGGCC G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:12:

TGGGGCTTCT ATCCAGCAGA A                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:13:

AATGTGCTCT ACCACACAGG T                                              21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:14:

CTGTGTGGTA GAGCACATTG G                                              21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:15:

TCGGGACTGG ACACCTGGGC T                                              21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:16:

AGGGTCTGCA TGGGGACAG C                                               21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:17:

GAGTGTAACT AGAGTGGCCA G                                              21

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:18:

GGACCCAGGA AGAGGAGTGT                                                20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single -continued (D) TOPOLOGY: linear (ii) MOLECULE TYPE: cDNA (iv) ANTI-SENSE: YES (xi) SEQUENCE DESCRIPTION: SEQ ID NO:19:

AGAGGCATGG TAGCATCATT G                                         21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:20:

TCCCCTATGT AAAACTTAGC A                                         21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:21:

GTCCTCTATG GCACACTGAG A                                         21

(2) INFORMATION FOR SEQ ID NO:22:

(i) SEQUENCE CHARACTERISTICS:
        (A) LENGTH: 1506 base pairs
        (B) TYPE: nucleic acid
        (C) STRANDEDNESS: double
        (D) TOPOLOGY: linear (ii) MOLECULE TYPE: cDNA (iv) ANTI-SENSE: NO (ix) FEATURE:
        (A) NAME/KEY: CDS
        (B) LOCATION: 369..1160
        (D) OTHER INFORMATION: /product= "DM Beta"

(xi) SEQUENCE DESCRIPTION: SEQ ID NO:22:

AGAATTAAGA GAGACAAGGA GACCTGTTGT CTAAGACTAA GGCAGGATGA CGTTTACCTA      60

GTAACTGATG ATGCTAGGCT GAGGCACTCA GTGATTTGTC TCTACATTTG TCCCTGCCTA     120

CCTAGCCAAT CTGTCCCTGT TTCGGACACT GGACTCCCGT GAGCTGGAAG GAACAGATTT     180

AATATCTAGG GGCTGGGTAT CCCCACATCA CTCATTTGGG GGGTCAAGGG ACCCGGGCAA     240

TATAGTATTC TGCTCAGTGT CTGGAGATCA TCTACCCAGG CTGGGGCTTC TGGGACAGGC     300

GAGGACCCAC GGACCCTGGA AGAGCTGGTC CAGGGGACTG AACTCCCGGC ATCTTTACAG     360

AGCAGAGC ATG ATC ACA TTC CTG CCG CTG CTG CTG GGG CTC AGC CTG GGC     410
         Met Ile Thr Phe Leu Pro Leu Leu Leu Gly Leu Ser Leu Gly
           1               5                  10

```
TGC ACA GGA GCA GGT GGC TTC GTG GCC CAT GTG GAA AGC ACC TGT CTG      458
Cys Thr Gly Ala Gly Gly Phe Val Ala His Val Glu Ser Thr Cys Leu
 15              20                  25                  30

TTG GAT GAT GCT GGG ACT CCA AAG GAT TTC ACA TAC TGC ATC TCC TTC      506
Leu Asp Asp Ala Gly Thr Pro Lys Asp Phe Thr Tyr Cys Ile Ser Phe
                 35                  40                  45

AAC AAG GAT CTG CTG ACC TGC TGG GAT CCA GAG GAG AAT AAG ATG GCC      554
Asn Lys Asp Leu Leu Thr Cys Trp Asp Pro Glu Glu Asn Lys Met Ala
             50                  55                  60

CCT TGC GAA TTT GGG GTG CTG AAT AGC TTG GCG AAT GTC CTC TCA CAG      602
Pro Cys Glu Phe Gly Val Leu Asn Ser Leu Ala Asn Val Leu Ser Gln
         65                  70                  75

CAC CTC AAC CAA AAA GAC ACC CTG ATG CAG CGC TTG CGC AAT GGG CTT      650
His Leu Asn Gln Lys Asp Thr Leu Met Gln Arg Leu Arg Asn Gly Leu
     80                  85                  90

CAG AAT TGT GCC ACA CAC ACC CAG CCC TTC TGG GGA TCA CTG ACC AAC      698
Gln Asn Cys Ala Thr His Thr Gln Pro Phe Trp Gly Ser Leu Thr Asn
 95                 100                 105                 110

AGG ACA CGG CCA CCA TCT GTG CAA GTA GCC AAA ACC ACT CCT TTT AAC      746
Arg Thr Arg Pro Pro Ser Val Gln Val Ala Lys Thr Thr Pro Phe Asn
                115                 120                 125

ACG AGG GAG CCT GTG ATG CTG GCC TGC TAT GTG TGG GGC TTC TAT CCA      794
Thr Arg Glu Pro Val Met Leu Ala Cys Tyr Val Trp Gly Phe Tyr Pro
            130                 135                 140

GCA GAA GTG ACT ATC ACG TGG AGG AAG AAC GGG AAG CTT GTC ATG CCT      842
Ala Glu Val Thr Ile Thr Trp Arg Lys Asn Gly Lys Leu Val Met Pro
            145                 150                 155

CAC AGC AGT GCG CAC AAG ACT GCC CAG CCC AAT GGA GAC TGG ACA TAC      890
His Ser Ser Ala His Lys Thr Ala Gln Pro Asn Gly Asp Trp Thr Tyr
160                 165                 170

CAG ACC CTC TCC CAT TTA GCC TTA ACC CCT TCT TAC GGG GAC ACT TAC      938
Gln Thr Leu Ser His Leu Ala Leu Thr Pro Ser Tyr Gly Asp Thr Tyr
175                 180                 185                 190

ACC TGT GTG GTA GAG CAC ATT GGG GCT CCT GAG CCC ATC CTT CGG GAC      986
Thr Cys Val Val Glu His Ile Gly Ala Pro Glu Pro Ile Leu Arg Asp
                195                 200                 205

TGG ACA CCT GGG CTG TCC CCC ATG CAG ACC CTG AAG GTT TCT GTG TCT     1034
Trp Thr Pro Gly Leu Ser Pro Met Gln Thr Leu Lys Val Ser Val Ser
                210                 215                 220

GCA GTG ACT CTG GGC CTG GGC CTC ATC ATC TTC TCT CTT GGT GTG ATC     1082
Ala Val Thr Leu Gly Leu Gly Leu Ile Ile Phe Ser Leu Gly Val Ile
            225                 230                 235

AGC TGG CGG AGA GCT GGC CAC TCT AGT TAC ACT CCT CTT CCT GGG TCC     1130
Ser Trp Arg Arg Ala Gly His Ser Ser Tyr Thr Pro Leu Pro Gly Ser
            240                 245                 250

AAT TAT TCA GAA GGA TGG CAC ATT TCC TAGAGGCAGA ATCCTACAAC           1177
Asn Tyr Ser Glu Gly Trp His Ile Ser
255                 260

TTCCACTCCA AGTGAGAAGG AGATTCAAAC TCAATGATGC TACCATGCCT CTCCAACATC   1237

TTCAACCCCC TGACATTATC TTGGATCCTA TGGTTTCTCC ATCCAATTCT TTGAATTTCC   1297

CAGTCTCCCC TATGTAAAAC TTAGCAACTT GGGGACCTC ATTCCTGGGA CTATGCTGTA    1357

ACCAAATTAT TGTCCAAGGC TATATTTCTG GGATGAATAT AATCTGAGGA AGGGAGTTAA   1417

AGACCCTCCT GGGGCTCTCA GTGTGCCATA GAGGACAGCA ACTGGTGATT GTTTCAGAGA   1477

AATAAACTTT GGTGGAAAAA AAAAAAAAA                                    1506

(2) INFORMATION FOR SEQ ID NO:23:
    (i) SEQUENCE CHARACTERISTICS:
```

(A) LENGTH: 263 amino acids
(B) TYPE: amino acid
(D) TOPOLOGY: linear (ii) MOLECULE TYPE: protein (xi) SEQUENCE DESCRIPTION: SEQ ID NO:23:

```
Met Ile Thr Phe Leu Pro Leu Leu Gly Leu Ser Leu Gly Cys Thr
 1               5                  10                  15

Gly Ala Gly Gly Phe Val Ala His Val Glu Ser Thr Cys Leu Leu Asp
            20                  25                  30

Asp Ala Gly Thr Pro Lys Asp Phe Thr Tyr Cys Ile Ser Phe Asn Lys
            35                  40                  45

Asp Leu Leu Thr Cys Trp Asp Pro Glu Glu Asn Lys Met Ala Pro Cys
 50                  55                  60

Glu Phe Gly Val Leu Asn Ser Leu Ala Asn Val Leu Ser Gln His Leu
 65                  70                  75                  80

Asn Gln Lys Asp Thr Leu Met Gln Arg Leu Arg Asn Gly Leu Gln Asn
                85                  90                  95

Cys Ala Thr His Thr Gln Pro Phe Trp Gly Ser Leu Thr Asn Arg Thr
                100                 105                 110

Arg Pro Pro Ser Val Gln Val Ala Lys Thr Thr Pro Phe Asn Thr Arg
                115                 120                 125

Glu Pro Val Met Leu Ala Cys Tyr Val Trp Gly Phe Tyr Pro Ala Glu
130                 135                 140

Val Thr Ile Thr Trp Arg Lys Asn Gly Lys Leu Val Met Pro His Ser
145                 150                 155                 160

Ser Ala His Lys Thr Ala Gln Pro Asn Gly Asp Trp Thr Tyr Gln Thr
                165                 170                 175

Leu Ser His Leu Ala Leu Thr Pro Ser Tyr Gly Asp Thr Tyr Thr Cys
                180                 185                 190

Val Val Glu His Ile Gly Ala Pro Glu Pro Ile Leu Arg Asp Trp Thr
                195                 200                 205

Pro Gly Leu Ser Pro Met Gln Thr Leu Lys Val Ser Val Ser Ala Val
        210                 215                 220

Thr Leu Gly Leu Gly Leu Ile Ile Phe Ser Leu Gly Val Ile Ser Trp
225                 230                 235                 240

Arg Arg Ala Gly His Ser Ser Tyr Thr Pro Leu Pro Gly Ser Asn Tyr
                245                 250                 255

Ser Glu Gly Trp His Ile Ser
                260
```